(12) United States Patent
Houston et al.

(10) Patent No.: US 9,632,030 B1
(45) Date of Patent: Apr. 25, 2017

(54) METHODS OF MEASURING FLUORESCENCE LIFETIME USING A FLOW CYTOMETER

(71) Applicant: Arrowhead Center, Inc., Las Cruces, NM (US)

(72) Inventors: Jessica P. Houston, Las Cruces, NM (US); Mark A. Naivar, Los Alamos, NM (US)

(73) Assignee: Arrowhead Center, Inc., Las Cruces, NM (US)

( * ) Notice: Subject to any disclaimer, the term of this patent is extended or adjusted under 35 U.S.C. 154(b) by 348 days.

(21) Appl. No.: 14/072,521

(22) Filed: Nov. 5, 2013

Related U.S. Application Data

(60) Provisional application No. 61/722,498, filed on Nov. 5, 2012.

(51) Int. Cl.
*G01N 33/48* (2006.01)
*G01N 21/64* (2006.01)
*G01N 15/14* (2006.01)
*G06G 7/58* (2006.01)

(52) U.S. Cl.
CPC ..... *G01N 21/6486* (2013.01); *G01N 15/1459* (2013.01); *G01N 15/1463* (2013.01)

(58) Field of Classification Search
CPC .............................. G06F 19/32; G06F 19/322
See application file for complete search history.

(56) References Cited

U.S. PATENT DOCUMENTS

| | | | |
|---|---|---|---|
| 5,196,709 | A | 3/1993 | Berndt et al. |
| 5,208,651 | A | 5/1993 | Buican |
| 5,270,548 | A | 12/1993 | Steinkamp |
| 5,315,122 | A | 5/1994 | Pinsky et al. |
| 5,317,162 | A | 5/1994 | Pinsky et al. |
| 5,485,530 | A | 1/1996 | Lakowicz et al. |
| 5,504,337 | A | 4/1996 | Lakowicz et al. |
| 5,909,278 | A | 6/1999 | Deka et al. |
| 6,426,505 | B1 | 7/2002 | Rao et al. |
| 7,054,002 | B1 | 5/2006 | Sevick-Muraca et al. |
| 7,822,558 | B2 | 10/2010 | Kimura et al. |
| 8,101,426 | B2 | 1/2012 | Durack |
| 8,330,124 | B2 | 12/2012 | Doi et al. |
| 8,389,291 | B2 | 3/2013 | Durack et al. |
| 8,415,627 | B2 | 4/2013 | Doi |
| 2003/0205682 | A1 | 11/2003 | Kapoor et al. |
| 2007/0096039 | A1 | 5/2007 | Kapoor et al. |
| 2010/0032584 | A1 | 2/2010 | Dayong et al. |
| 2011/0176127 | A1 | 7/2011 | Kanda et al. |

OTHER PUBLICATIONS

Begole, "Application of the Cubic Spline Function in the Description of Dental Arch Form", Journal of Dental Research, 1975, 1549-1556.

Behforooz, et al., "End Conditions for Cubic Spline Interpolation", Journal of Applied Mathematics, 1979, 355-366.
Brumback, et al., "Smoothing Spline Models for the Analysis of Nested and Crossed Samples of Curves", Journal of the American Statistical Association, Sep. 1998, 961-976.
Constantinides, et al., "Numerical Methods for Chemical Engineers with MATLAB Applications", 1999.
Dubelaar, et al., "CytoBuoy: a step forward towards using flow cytometry in operational oceanography", Sicnetia Marina, 2000, 255-265.
Eyal, et al., "Velocity-independent microfluidic flow cytometry", Electrophoresis, 2002, 2653-2657.
Godavarti, et al., "Automated Particle Classification Based on Digital Acquisition and Analysis of Flow Cytometric Pulse Waveforms", Cytometry, 1996, 330-339.
Goddard, et al., "Single Particle High Resolution Spectral Analysis Flow Cytometry", Cytometry A, 2006, 842-851.
Halang, et al., "Cubic Spline Interpolation for the Calculation of Retention Indices in Temperature-Programmed Gas-Liquid Chromatography", Analytical Chemistry, Nov. 1978, 1829-1832.
Hou, et al., "Cubic Splines for Image Interpolation and Digital Filtering", IEEE Transactions on Acoustics, Speech, and Signal Processing, Dec. 1978, 508-517.
Houston, et al., "Capture of Fluorescence Decay Times by Flow Cytometry", Current Protocols in Cytometry, Jan. 2012, 1.25.1-115. 21.
Jupp, "Fitting Smooth Paths to Spherical Data", Applied Statistics, 1987, 34-46.
Kastanek, et al., "Description of Soil Water Characteristics Using Cubic Spline Interpolation", Soil Science Society of America Journal, Mar.-Apr. 2001, 279-283.
Naivar, et al., "Open, Reconfigurable Cytometric Acquisition System: ORCAS", Cytometry A, 2007, 915-924.
Reinsch, "Smoothing by Spline Functions", Numerische Mathematik, 1967, 177-183.
Rubin, et al., "Viscous Flow Solutions with a Cubic Spline Approximation", Computers and Fluids, 1975, 1-36.
Steinkamp, et al., "Resolution of Fluorescence Signals From Cells Labeled With Fluorochromes Having Different Lifetimes by Phase-Sensitive Flow Cytometry", Cytometry, 1993, 210-216.
Sun, et al., "Digital signed processing methods for impedance microfluidic cytometry", Microfluid Nanofluid, 2008, 179-187.
Zilmer, et al., "Flow Cytometric Analysis Using Digital Signal Processing", Cytometry, 1995, 102-117.

(Continued)

*Primary Examiner* — Eric S Dejong
(74) *Attorney, Agent, or Firm* — Janeen C. Vilven-Doggett; Peacock Myers, P.C.

(57) ABSTRACT

A method for determining fluorescent lifetime of a fluorescent particle in a flow cytometer comprising calculating a point on a digitized scatter waveform and a corresponding point on a digitized fluorescence waveform using the same method and calculating the time delay if any between the calculated point on the digitized scatter waveform and the calculated point on the fluorescent waveform to determine the fluorescent lifetime of the fluorescent particle with digitized data collected from a flow cytometer having an unmodulated light source.

19 Claims, 16 Drawing Sheets

(56) References Cited

OTHER PUBLICATIONS

Cao, R. et al., "Fluorescence Lifetime Acquisition with Non-Modulated Cytometric Waveforms", Poster, XXVI Congress for the International Society for the Advancement of Cytometry, Baltimore, Maryland, May 2011.

Deka, Chiranjit et al., "Fluorescence Lifetime Measurements in a Flow Cytometer by Amplitude Demodulation Using Digital Data Acquisition Technique", Cytometry, vol. 17, Wiley-Liss, Inc., 1994, 94-101.

Houston, Jessica P. et al., "Digital Analysis and Sorting of Fluorescence Lifetime by Flow Cytometry", Cytometry Part A, vol. 77A, 2010, 861-872.

Pinsky, Bertram G. et al., "Phase-Resolved Fluorescence Lifetime Measurements for Flow Cytometry", Cytometry, vol. 14, Wiley-Liss, Inc., 1993, 123-135.

Steinkamp, John A., "Fluorescence Lifetime Flow Cytometry", Emerging Tools for Single-Cell Analysis: Advances in Optical Measurement Technologies, Ed. by Gary Durack, J. Paul Robinson, Wiley-Liss, Inc., 2000, 175-196.

Steinkamp, John A. et al., "Resolution of Fluorescence Signals from Cells Labeled with Fluorochromes Having Different Lifetimes by Phase-Sensitive Flor Cytometry", Cytometry, vol. 14, Wiley-Liss, Inc., 1993, 210-216.

| Fluorescent dye | Mean (ns) | Calibrated Mean (ns) | Standard Deviation (ns) |
|---|---|---|---|
| Fluorescein isothyocyanate | 7.832 | 4.0 | 13.125 |
| Phycoerythrin | 5.989 | 2.157 | 13.926 |
| Propidium iodide | 21.181 | 17.349 | 12.362 |

FIG. 11

METHODS OF MEASURING FLUORESCENCE LIFETIME USING A FLOW CYTOMETER

CROSS-REFERENCE TO RELATED APPLICATIONS

This application claims priority to and the benefit of the filing of U.S. Provisional Patent Application Ser. No. 61/722,498, entitled "Methods of Measuring Fluorescence Lifetime Using a Flow Cytometer", filed on Nov. 5, 2012, and the specification and claims thereof are incorporated herein by reference.

STATEMENT REGARDING FEDERALLY SPONSORED RESEARCH OR DEVELOPMENT

This invention was made with government support under Contract No. DBI-0964127 awarded by the National Science Foundation. The government has certain rights in the invention.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

Field of the Invention (Technical Field)

The present invention relates to methods of measuring a fluorescence lifetime on a standard flow cytometer without modulating the excitation light source. As a particle, for example cell, passes through the interrogation point of a flow cytometer it scatters light and any fluorophores on or in the cell will absorb the incident light and emit photons in a range of wavelengths. These photons terminate at a detector and a current is generated in the detector proportional to the amount of incident light. This process is repeated for each cell and for every laser employed on the instrument.

A standard flow cytometer consists of a fluidics system into which a sample comprising particles to be interrogated is delivered. The particles are focused single file in a stream of flowing particles and carried to an interrogation point or flow cell. The flow cell includes an optics system to focus excitation light from a light source, for example an unmodulated laser, onto the focused stream and to collect the emission from the individual particles as the particles flow single file through the flow cell having one or more optical detectors to convert the collected optical emissions from each particle into electrical signals, and electronics to analyze these electrical signals to determine the optical response of each particle. In some forms the flow cytometer may use electromagnetic energy in lieu of or in combination with a light source. In some forms, the signals from the optical detectors are digitized before being processed. In some forms, the analog to digital converters (ADCs) used to digitize the signals are phase locked.

The fluorescence lifetime is a photophysical property of a fluorescent molecule. It can be a reporter of different phenomena when the fluorophore is used in a cellular context. This is because the fluorescent lifetime of a molecule changes based on biochemical changes in a microenvironment that surrounds the fluorophore itself. For example, the fluorescence decay might change if the fluorophore is bound or unbound, is near a quencher, if there are temperature changes, and/or if there are local pH changes surrounding the fluorophore. Also, the lifetime of a fluorescent protein can change if it undergoes conformational changes, if its quantum yield is changed, if it is fused to another protein, if it is exposed or not to quenchers in lipid bilayers, if there are perturbations of the protein structure itself, and/or if there are impacting solutes and/or analytes in the nucleus or cytoplasm. All of these can occur in different contexts such as, but not limited to, with cell cycle changes, with changes in the fixation or viability status of a cell, when the cell is treated with chemicals, when there are genetic modifications introduced into the cell, combinations thereof and the like.

Current methods for measuring fluorescence lifetime in flow cytometry require the modulation of the excitation light source (typically a laser) in order to measure the temporal response of the fluorophore. This requires high frequency modulation of the light source, and/or high bandwidth amplifiers, and/or analog electronics, and either high bandwidth analog signal processing circuitry or a high speed analogue to digital converter (ADC).

Measuring fluorescent lifetime is useful for addressing the following:

(1) Autofluorescence Issues.

Because of spectral autofluorescence interference with fluorescent protein expression, many cytometrists have difficulty identifying the expression of their gene of interest. Most individuals seek compensation but also find that difficult or do not understand how autofluorescence may or may not impact compensation. In particular, cells that have a high amount of autofluorescence are alveolar macrophages, microglia, eosinophil, and neutrophils. However, all cells have a considerable amount of autofluorescence signals. Moreover, there are groups that need to fix the cells in order to understand more about the internally tagged proteins, antigens, nucleic acids, organelles, and the like. Fixation dramatically impacts the level of autofluorescence in the cell. A method of fluorescent lifetime determination according to one embodiment of the present invention can discriminate the background autofluorescence from the dim exogenous fluorescence.

(2) Broad Emission of Organic Fluorophores.

Issues are always present when cytometry users seek greater than 6 color staining protocols in cytometry. For example, there are always issues with spectral overlap of the range of phycoerythrin tandem dyes (e.g., PE-Cy5 vs. APC). Many fluorophores spectrally overlap and it is hard to discriminate between their colors. Compensation is performed to account for the "bleed-through" of different colors into different photodetectors. Yet compensation often confuses the average cytometrists.

(3) Rare Event Detection.

Currently many groups are using cytometry for "cleaning," sorting, filtering, and discovering single cell organisms. For example, in the field of marine biology, cytometrists are exploring rare single-cell species from among large-body water samples. Also, in the renewable energy sector, researchers have a need to sort particular algae cells from among a large population of bacterium to extract biodiesel. Also, different industries use cytometry for quality control to check the counts of bacterium. With applications like these that do not utilize exogenous stains, lifetime measurements are beneficial because it is independent of the intensity.

(4) Quantitative Flow Cytometry.

Investigators utilize Forster resonance energy transfer "FRET" to look at protein-protein interactions as well as intracellular signaling events. This is typically done with fluorescent proteins. In this work, FRET, or loss of FRET is used to indicate the binding or interaction of two proteins. Cytometers can measure FRET with intensity changes but it is less quantitative. The only way to definitively assure that interaction is occurring at a given concentration is through the fluorescence lifetime measurement.

(5) Design of Novel Fluorescent Proteins.

There is continuous research occurring on the development of fluorescent proteins. Investigators are exploring ways to make proteins brighter and more stable. The fluorescence lifetime can be an indicator of quantum yield and a sorting cytometer can sort based on the lifetime parameter.

Currently no standard cytometer is capable of measuring the fluorescence lifetime as a single parameter.

BRIEF SUMMARY OF THE INVENTION

One embodiment of the present invention provides a method for determining fluorescent lifetime of a fluorescent particle in a flow cytometer. The method includes detecting at a first detector a scatter signal and detecting at a second detector a fluorescent signal from a fluorescent particle as the fluorescent particle transits over time through an interrogation beam of a non-modulated light source in the flow cytometer wherein the first detector and the second detector are temporally phase locked. The signal from the first detector and the signal from the second detector are digitized to produce a digitized scatter waveform and a digitized fluorescence waveform for the particle. A point on the digitized scatter waveform and a corresponding point on the digitized fluorescence waveform is calculated using the same method. The time delay if any between the calculated point on the digitized scatter waveform and the calculated point on the fluorescence waveform is calculated wherein the time delay is the fluorescent lifetime of the fluorescent particle.

Another embodiment of the present invention provides a method for determining fluorescent lifetime variation between a first fluorescent particle and second fluorescent particle in a flow cytometer. The method includes detecting at a first detector a scatter signal and detecting at a second detector a fluorescent signal from a first fluorescent particle and second fluorescent particle as the first fluorescent particle and the second fluorescent particle transits over time through an interrogation beam of a non-modulated light source in the flow cytometer wherein the first detector and the second detector are temporally phase locked and wherein a first set of scatter signal and fluorescent signal is generated for the first fluorescent particle and a second set of scatter signal and fluorescent signal is generated for the second fluorescent particle. The signal from the first detector and the signal from the second detector for the first fluorescent particle and the second fluorescent particle are digitized to produce a digitized scatter waveform and a digitized fluorescence waveform for the first fluorescent particle and the second fluorescent particle. A point on the digitized scatter waveform and a corresponding point on the digitized fluorescence waveform is calculated using the same method for the first set of digitized scatter signal and fluorescent signal and the second set of digitized scatter signal and fluorescent signal. The time delay if any between the calculated point on the digitized scatter waveform and the calculated point on the fluorescent waveform of the first fluorescent particle is calculated wherein the time delay is the fluorescent lifetime of the first fluorescent particle. The time delay if any between the calculated point on the digitized scatter waveform and the calculated point on the fluorescent waveform of the second fluorescent particle is calculated wherein the time delay is the fluorescent lifetime of the second fluorescent particle. The information about the fluorescent lifetime of the second fluorescent particle as compared to the fluorescent lifetime of the first fluorescent particle is provided to the system.

Another embodiment of the present invention provides for a non-transitory computer readable medium containing program instructions for determining fluorescent lifetime variation between a first fluorescent particle and second fluorescent particle in a flow cytometer wherein the instructions by one or more processors of a computer include code for obtaining a digitized scatter waveform and a digitized fluorescence waveform for a first fluorescent particle to create a first set of digitized data and obtaining a digitized scatter waveform and a digitized fluorescence waveform for a second fluorescent particle to create a second set of digitized data; code for calculating a point on the digitized scatter waveform and a corresponding point on the digitized fluorescence waveform using the same method for the first set of digitized scatter signal and fluorescent signal and the second set of digitized scatter signal and fluorescent signal; code for calculating the time delay if any between the calculated point on the digitized scatter waveform and the calculated point on the fluorescent waveform of the first fluorescent particle to determine the fluorescent lifetime of the first fluorescent particle; code for calculating the time delay if any between the calculated point on the digitized scatter waveform and the calculated point on the fluorescent waveform of the second fluorescent particle to determine the fluorescent lifetime of the second fluorescent particle; and code for providing information regarding the fluorescent lifetime of the second fluorescent particle as compared to the lifetime of the first fluorescent particle.

In a preferred embodiment, calculating the point on the digitized scatter waveform and the point on the digitized fluorescence waveform comprises calculating the area of each digitized waveform where the area reaches 50% of the total area for each waveform to determine a 50% point. In another preferred embodiment, calculating a point on the digitized scatter waveform and calculating the point on the digitized fluorescence waveform comprises calculating the steepest location on the rising edge and falling edge of each waveform with the location in between to determine a peak time point.

In an embodiment disclosed here the scatter is a side scatter signal or a forward scatter signal. Digitizing the signal may include an analogue to digital conversion. The fluorescent lifetime may include a plurality of fluorescent lifetimes from a plurality of fluorophores on or within the fluorescent particle. A fluorescent lifetime may be derived from autofluorescence of the particle or a fluorophore associated therewith. The particle may be a cell. The detector may be a photo multiplier tube.

One aspect of one embodiment of the present invention provides for the direct digitization of original waveforms generated from photodetectors of a standard flow cytometer.

Another aspect of one embodiment of the present invention provides for acquisition of a full pulse signal which can be manipulated to obtain fluorescent lifetime value for a fluorescent particle in flow cytometry.

An aspect of the present invention comprises a method for easily acquiring a fluorescence lifetime in a cytometer without the need to do complex modulation approaches and/or in the absence of a modulated laser.

One aspect of an embodiment of the present invention is to measure small delays (on the order of nanoseconds) on relatively wide pulses (on the order of microseconds) from a particle with a non-modulated laser in a standard flow cytometer.

One aspect of the present invention provides for determining fluorescent lifetimes of each fluorophore and discriminating fluorescent signals that overlap. Yet another aspect of an embodiment of the present invention provides for determination of fluorescence lifetime in flow cytometry for use in one or more of the following autofluorescence compensation, discriminating fluorescent signal overlap, detecting rare events, quantitative flow cytometry, and novel fluorescent protein design.

Another aspect of one embodiment of the present invention provides a new solution in cytomics permitting others to accomplish high throughput analysis with the fluorescence lifetime as a parameter in a flow cytometer which does not modulate the laser light. Another aspect of embodiments of the present invention provides for a novel approach to discriminate the degree of spectral overlap in view of the current range of fluorescent dyes.

Further scope of applicability of the present invention will be set forth in part in the detailed description to follow, taken in conjunction with the accompanying drawing, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIG. 11 is a table of results from the fluorescent particle study with fluorescent lifetime calculated according to one embodiment of the present invention.

DETAILED DESCRIPTION OF THE INVENTION

An embodiment of the present invention comprises a data acquisition and processing system that digitizes the amplified signals from multiple detectors (for example photo multiplier tubes "PMT"s) and captures correlated. The amplified signals are generated when the optical signals are converted into electrical signals and amplified using an electronics module called a preamp. A waveform set is collected (one waveform for scatter and one waveform for fluorescence from each detector for a digitized signal) for each particle/cell that is analyzed. The waveform set for each particle can be processed as the sample is running, or saved for repeated processing afterwards. The system can use C++ or MATLAB to implement the signal processing algorithms but is not limited thereto.

Figure 14:
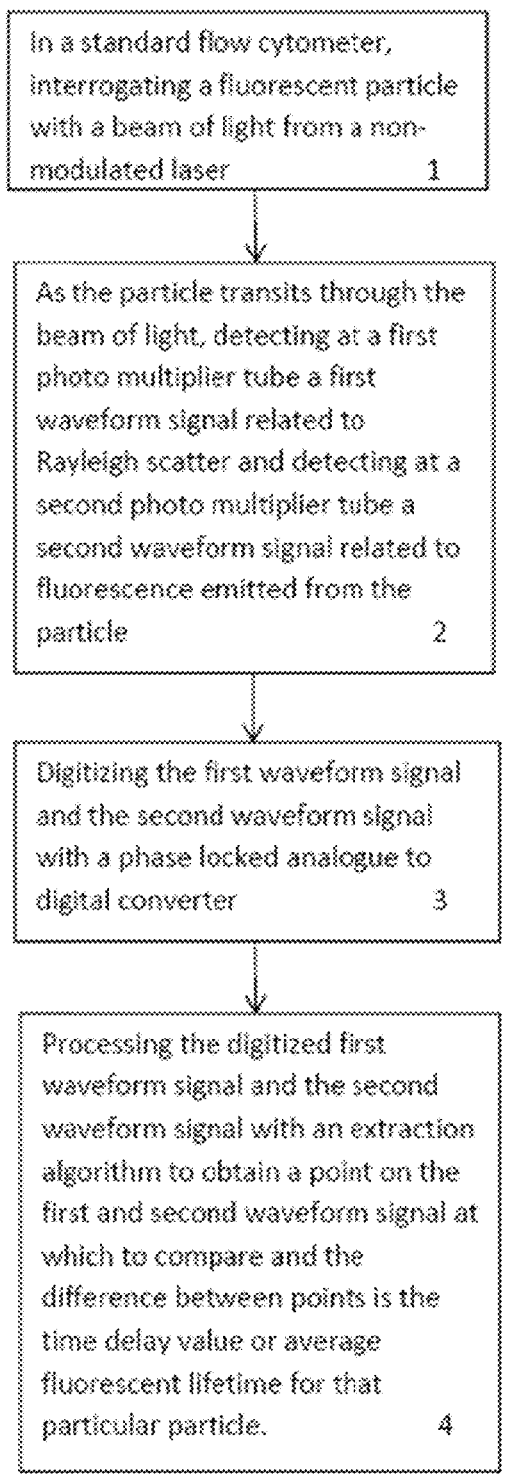
FIG. 14 illustrates a flow diagram of a method for determining the fluorescent lifetime of one embodiment of the present invention.

Embodiments of the current invention use methods of processing the signals to extract the fluorescent lifetime of the digitized signal. A method according to one embodiment of the present invention is illustrated in FIG. 14 and includes measuring a well-defined point on a fluorescence waveform and a scatter (from any angle) waveform and comparing the points between scatter and fluorescence detectors 4. The time difference between the point on the scatter waveform as compared to the point on the fluorescence waveform is the measured time delay. The measured time delay is proportional to the fluorescence lifetime. One method to identify the point on each waveform determines where the area of the pulse reaches 50% of the total area for each waveform, which can be thought of as the center of mass of the pulse. An alternative method determines the center point between the steepest rising and falling edges for each waveform. The difference between the two waveforms at the point calculated is the time delay or fluorescent lifetime.

Flow cytometry sorting and analysis is largely based upon the digitization of signals and subsequent collection of a small set of features (i.e. peak, area, width) that are extracted from full Gaussian-like waveforms. Such waveforms result when a photodetector observes signals such as Rayleigh scatter or fluorescence coming from a particle's passage through a finely focused laser beam. Owing to recent advances in data acquisition, embodiments of the present invention comprise methods to extract data and parameters that are otherwise hidden in the full Gaussian-like waveforms collected with a standard flow cytometer which parameter results in detecting of photodynamic properties of a fluorescence label.

An embodiment of the present invention comprises a method for capturing high-resolution waveforms from photodetectors that collect fluorescence signals in a flow cytometer. The cytometer can capture, preferably with precise temporal accuracy, an entire waveform which can then be used to extract fluorescence lifetime information with one or more digital signal processing methods. Implementation of the method with a flow cytometer requires that current and standard data systems be replaced (or modified) in order to capture and process the waveforms. This system and method exploits the fact that as a cell and/or particle flows past a focused laser spot, the particle is subjected to changes in light intensity, which are similar to a modulated laser. As the particle enters the laser, it experiences an increase in the light intensity which is similar to the rising edge of a modulated light source. As the particle leaves the laser, it experiences a decrease in the light intensity which is similar to the falling edge of a modulated light source. The measured fluorescence signals comprise time delay information, even when no laser modulation is being performed. Moreover, with a data processing system as disclosed herein, the time delay between the fluorescence waveform and the scatter waveform can be extracted and an additional parameter calculated for use in flow cytometry, e.g., the fluorescence lifetime of the fluorophore. In order to preserve the temporal information when capturing the signals from the detectors, the detectors are temporally phase locked.

An embodiment of the present invention preferably comprises a method for determining a fluorescent lifetime from one or more particles in a flow cytometer with an unmodulated laser as shown in FIG. 14. The method comprises flowing a particle past an unmodulated laser (1); phase-locking the capture of digital waveforms from signals detected at a detector that detects scatter and a detector that detects fluorescence to preserve the temporal information between the signals from different detectors (2) and (3) Determining the fluorescent lifetime from the captured signals representing scatter and fluorescence 4. The step of determining the fluorescent lifetime may further comprise measuring the time delay from a point on the scatter waveform as compared to the point on the fluorescence waveform wherein a point is identified by 1) calculating the area of the pulse from a particle as captured at the detector wherein the point represents 50% of the total area or 2) calculating a point from a particle between the steepest rising and falling edge of the pulse of a particle as captured at the detector.

Embodiments of the present invention operates with the signal detected by a PMT emitted from a particle traveling in a flow cytometer and interrogated with a laser light. A system and method as disclosed herein detects a particle and a fluorescent profile associated therewith in addition to the scatter of the laser light from the cells in order to measure the fluorescence lifetime without modulating the laser. Suspended particles, for example cells, traveling in a flow cytometer flow past a focused laser spot in optical communication with a PMT in a flow cytometer. These cells experience a rapid change in excitation intensity as they traverse the focused laser spot.

The emission or optical signals the excited cells generate is a short pulse. The pulse is translated into an electrical signal upon detection by the PMT. The waveform is the digitized electrical signal. The digitized signal typically has a Gaussian shape (see FIG. 1A). Under typical flow velocities and laser spot sizes, the cell traverses the laser spot within a few microseconds. Laser light that is scattered off of these cells and detected as a signal at a first PMT has no delay imparted on it, whereas the fluorescence pulse emitted from the same cell and detected as a signal at second PMT will be delayed due to the fluorescence lifetime. By measuring the time delay between a light scatter signal and a fluorescence signal, we can measure the lifetime of fluorophores on the cell (See FIG. 1B). In this way, we are able to measure fluorescence lifetime with a typical flow cytometer by simply changing the way the signals from the detectors are processed.

Figure 1A:
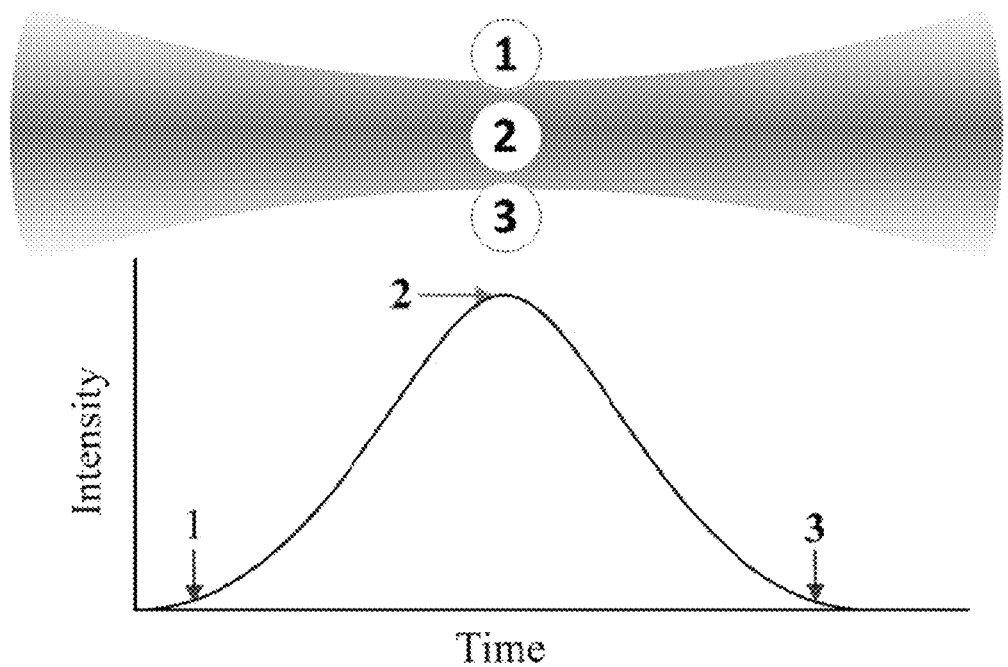
FIG. 1A illustrates a particle path through a laser spot and the corresponding time vs. intensity Gaussian waveform generated.
Figure 1B:
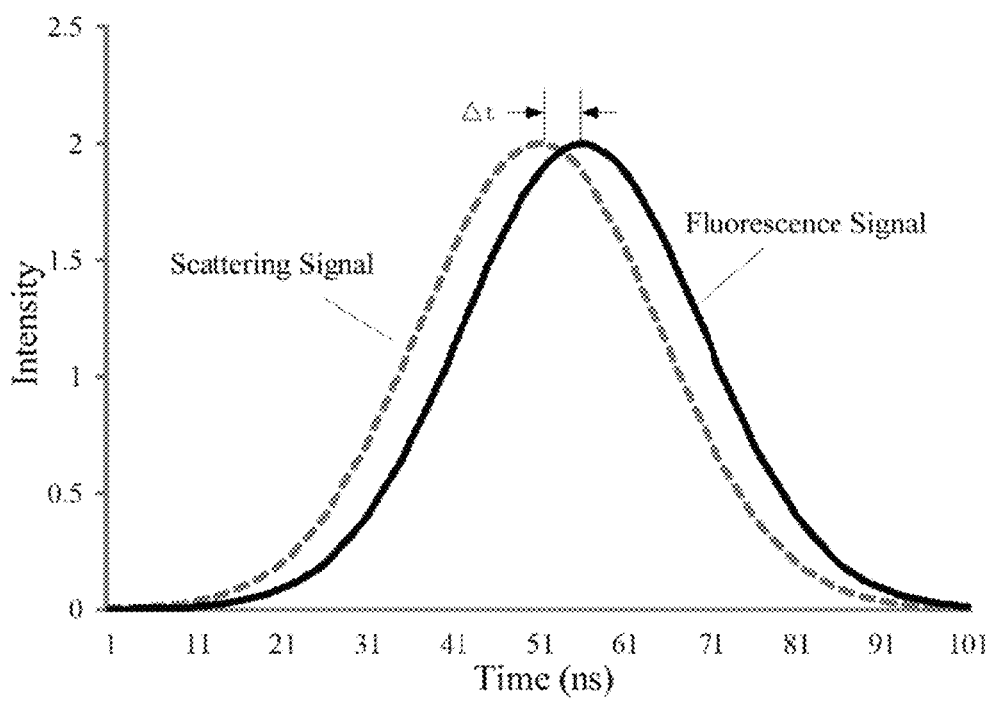
FIG. 1B illustrates a time vs. intensity graph of scatter signal vs. fluorescence signal.
Figure 1C:
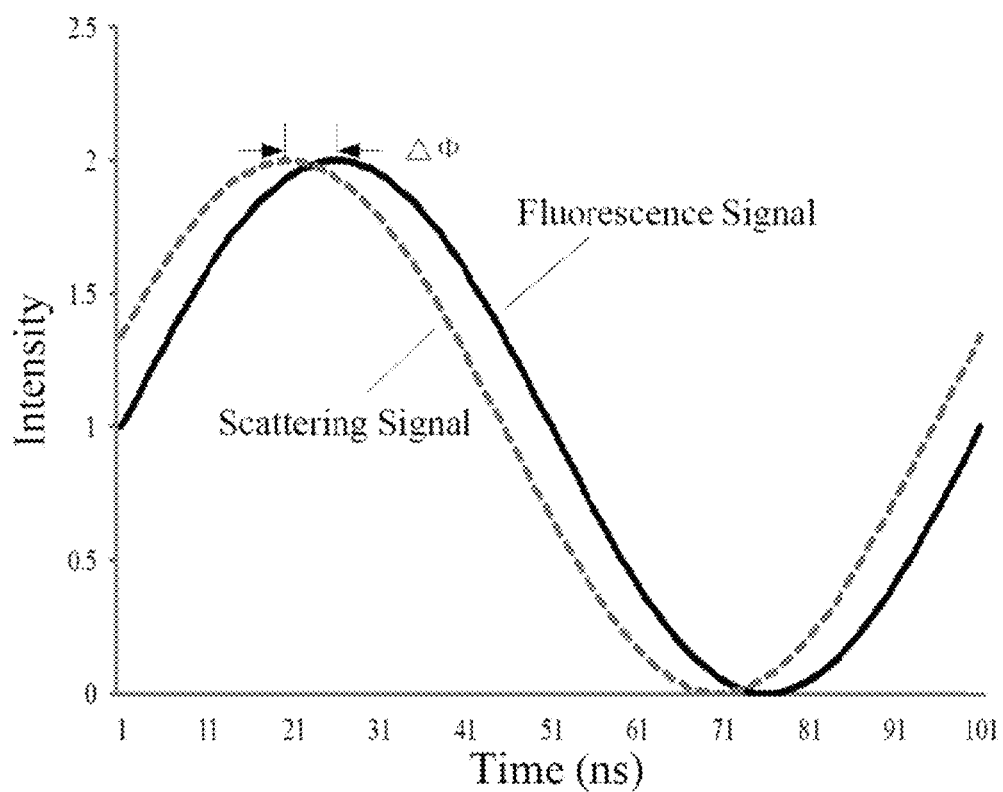
FIG. 1C illustrates a time vs. intensity graph of scatter signal vs. fluorescence signal.
Figure 10:
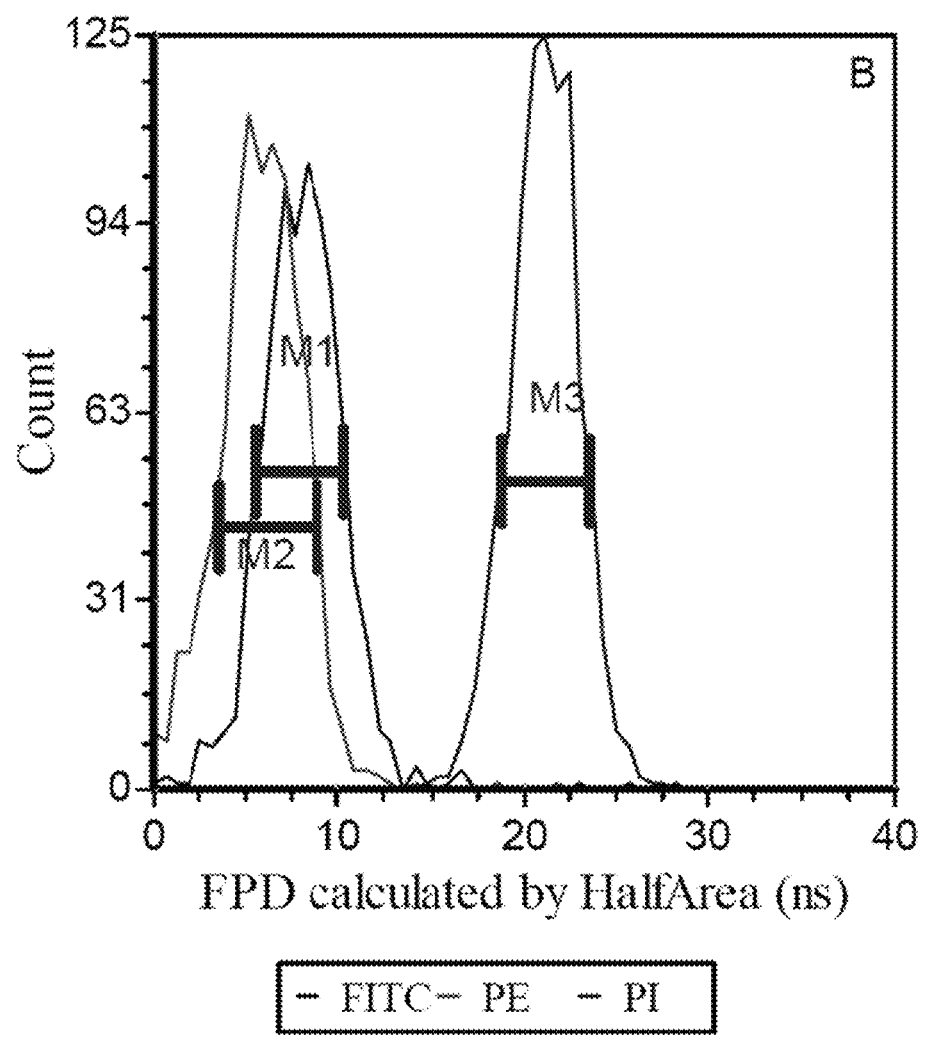
FIG. 10 is a histogram of delay values calculated when actual fluorescent particles were labeled with three different fluorescent molecules: M1 (fluorescein isothyocyanate), M2 (phycoerythrin), and M3 (propidium iodide). In these results the half-area algorithm was used.

Referring now to FIG. 1A, Gaussian-like pulses are generated in flow cytometry. A fluorescent particle transits the laser from position 1, through position 2 to position 3. The fluorescence emission and Rayleigh scattered light accordingly increases and reaches a peak at position 2, then decreases as the cell or particle leaves the excitation source from position 2 to position 3. FIG. 1B is an illustration of how the time delay will occur between scattering and fluorescence. The two pulses that are shown are delayed in time relative to each other and this time delay value, At, can be related to the average fluorescence lifetime. FIG. 10 shows a sinusoidal waveform, which is the traditional modulation signal used in standard fluorescence lifetime measurements in flow cytometry. The measured sinusoidal signals from scatter and fluorescence detectors are illustrated here to compare the differences in extracting the non-modulated time delay value relative to a modulated signal, phase-delay value (indicated by delta $\Delta$phi).

Figure 2:
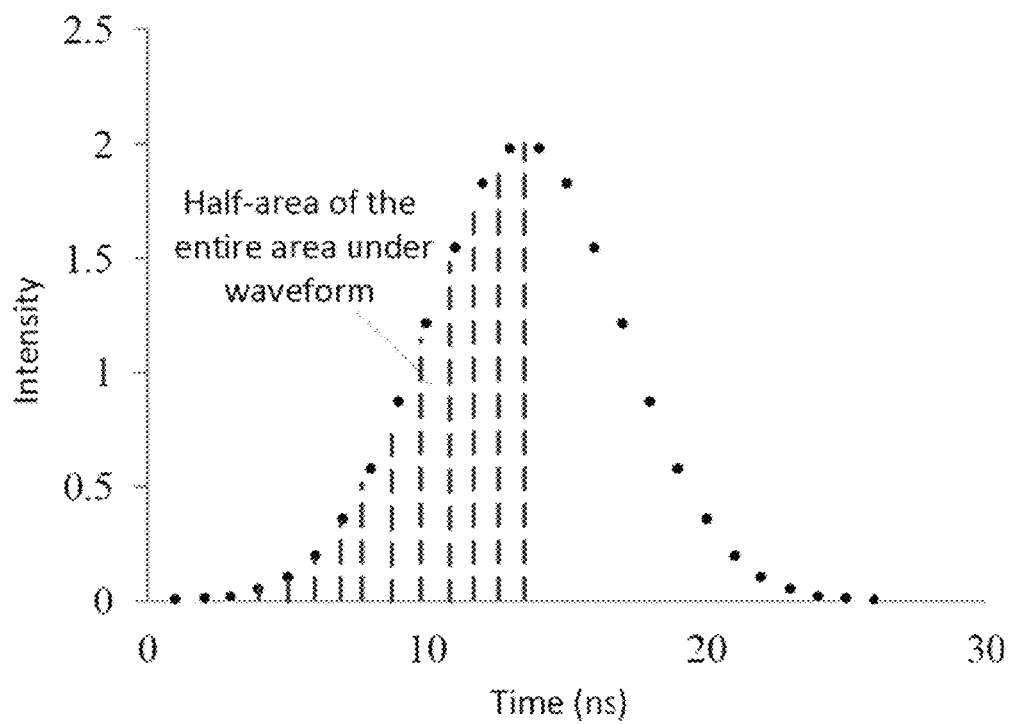
FIG. 2 illustrates a digital waveform and a 'half-area' method for extracting the center of the waveform according to one embodiment of the present invention.

Referring now to FIG. 2, a graph of intensity vs. time is illustrated for a waveform. The time delay is calculated using the half-area signal processing algorithm. The precise temporal location when the area reaches 50% is used as the center (or more precisely the center of mass) of the waveform, and the difference between the centers of the scatter and fluorescence waveforms are used as the time delay. The center location can be interpolated between samples which results in a resolution less than the time between samples. This increased resolution is required to achieve the accuracy needed to measure fluorescence lifetimes.

Figure 3:
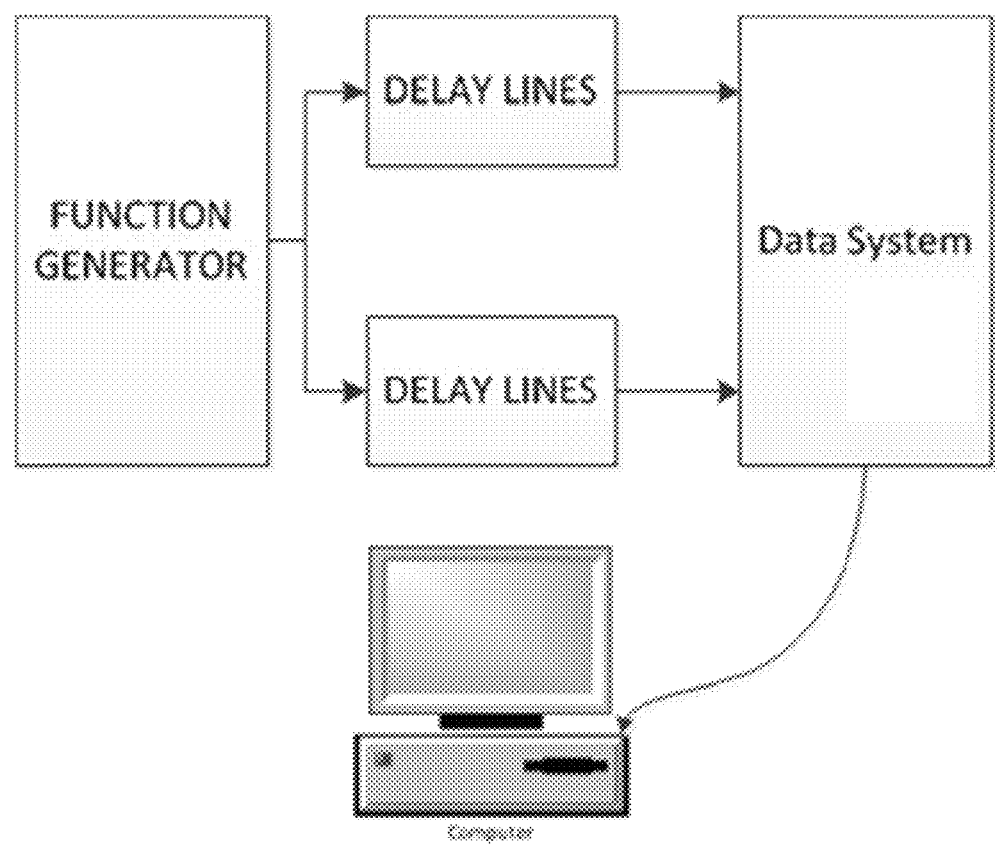
FIG. 3 illustrates an embodiment of a test system using delay lines.

Referring now to FIG. 3, a standard function generator generates a synthetic Gaussian pulse which is split and sent through two separate standard delay lines. The delay lines are inserted to introduce varying time delays between the two pulses to mimic the delay between a scatter and fluorescence signal that would be measured in a real flow cytometer. The synthetic and delayed waveforms are then recorded by the high speed data acquisition system for off-line analysis to calculate the time delays.

Figure 4:
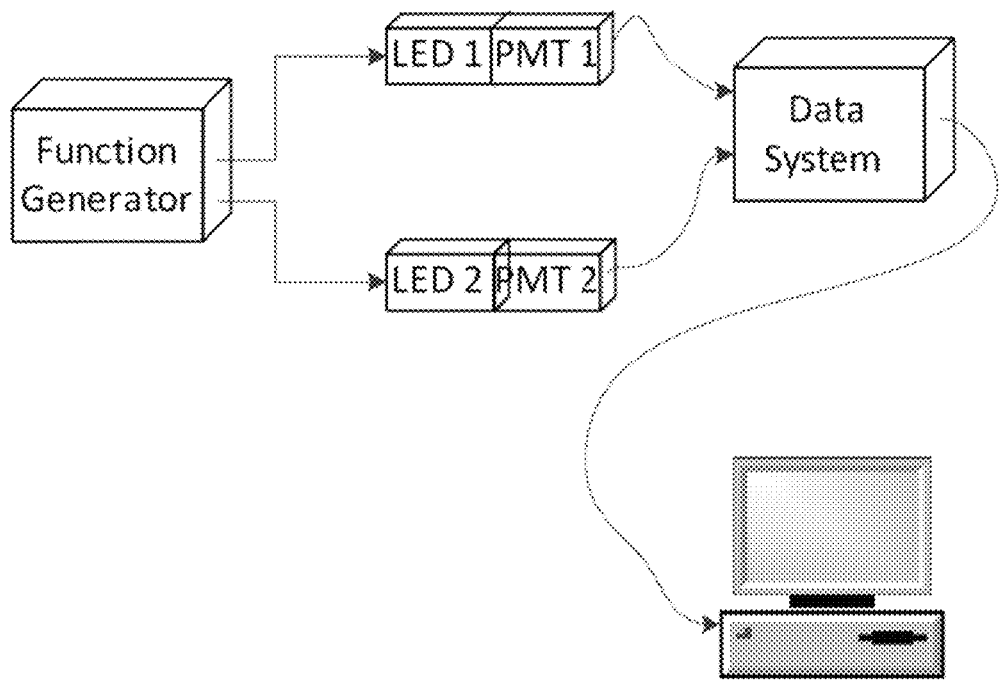
FIG. 4 illustrates an embodiment of a test system using optical detectors.

Referring now to FIG. 4, a pseudo-cytometry system using light emitting diodes (LEDs) is illustrated. Two identical LEDs are pulsed using a function generator. The function generator pulses each LED at the exact same repetition rate and imparts a delay between the pulses for each LED to simulate a delay between two optical signals. The LED light output from each source was focused (diffusely) onto two separate but identical PMT windows. No light attenuation was performed. By directing light signals onto each PMT, false cytometric pulses were generated with very low noise. Each PMT output was preamplified with identical hardware and digitized by a high speed data acquisition system. After collection of the full waveforms off-line analyses can be performed with algorithms that calculate the time delays.

Figure 5:
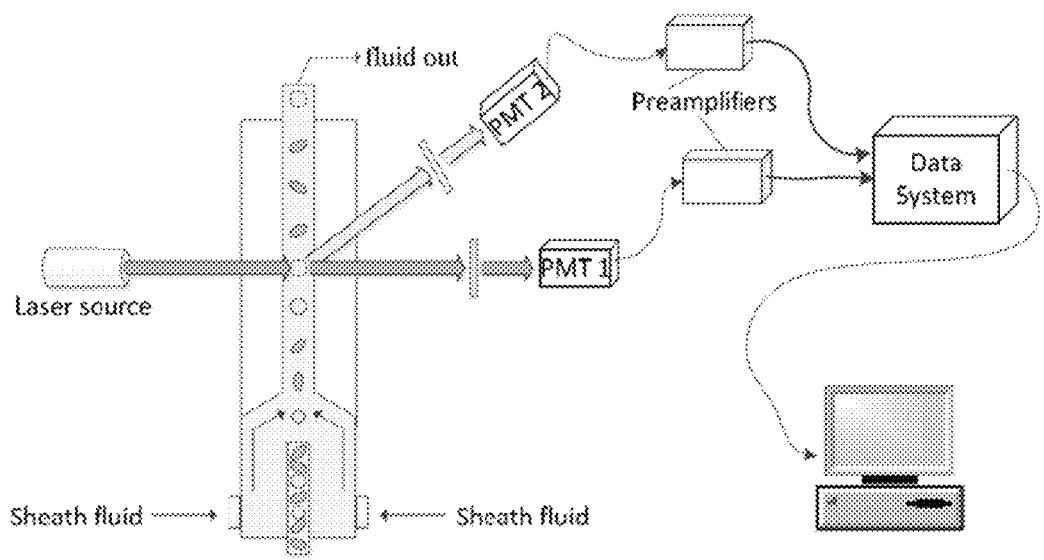
FIG. 5 is an embodiment of the present invention where an example flow cytometer is illustrated to capture fluorescence and side scatter from cells or particles.

Referring now to FIG. 5, an embodiment of the present invention is illustrated wherein a standard flow cytometer is illustrated to capture fluorescence and side scatter from cells or particles. In this illustration a laser is shown to excite small fluorescence microspheres (yellow and green ovals). Sheath fluid (saline water) is injected to help force the particles through the laser one-by-one. The photodetector that collects scattered light is labeled as PMT 1 and the fluorescence channel is labeled as PMT 2. Both of the collected optical signals are digitized with a high-speed data system. After collecting and recording the waveforms, an algorithm can be applied to calculate the time delay between scattered light and the fluorescence signal.

Embodiments of the present invention comprise methods of measuring fluorescence lifetime on a standard flow cytometer without requiring any modifications to the optics, fluidics or the detectors. In flow cytometry, any given fluorophore has a fluorescence that is similar in color to other fluorophores. Thus, to overcome overlap, fluorescence lifetime measurements and advanced detection methods can determine the time a fluorophores spends in an excited state. This excited state comprises a residence time that amounts to single to tens of nanosecond (ns). This residence time is the "fluorescence lifetime" and can be used to differentiate between fluorophores having the same or similar colors. Signal processing algorithms are used to accurately extract these small delays from the signals detected by the PMT.

A non-modulated lifetime cytometer allows cytometrists to measure not only the amount of fluorescence intensity from their cell or particle, but also the time it takes for that fluorescence to decay. It alleviates issues of spectral overlap among fluorophores, because each fluorophore has a unique fluorescence lifetime. Current commercial cytometers can capture and process high resolution waveforms from multiple detectors. A system of the present invention preferably uses a phase-locked ADCs to capture the waveforms in order to preserve the relative timing information. The signal processing algorithms extract the time delay information from the captured signals.

In embodiments of the present invention, different algorithms (are used on waveforms collected with a high-speed digital data system. The waveforms can be both artificially generated as well as collected from fluorescently-labeled cells and microspheres. In one embodiment of the present invention, a method was used (1) to determine if the fluorescence decay time of a fluorophore can be obtained simply by artificially introducing delays between the two Gaussian signals as well as measuring the actual delay caused by the fluorescence process using microspheres. Although methods to waveform processing are described herein, the present invention is not limited to these approaches, as there are other digital signal processing methods for parameter extraction.

Examples

Two algorithms are described (FIG. 12 and FIG. 13) and utilized as examples to extract fluorescent lifetimes of particles whose full waveforms are detected in a flow cytometer in the examples discussed herein. The algorithms include an algorithm that calculates the area under the pulse and divides that in half to determine the peak for the pulse-delay calculation FIG. 13; and an algorithm that calculates the steepest location on the rising edge of the pulse to locate the exact half-way point to identify the peak time (FIG. 13) these processing methods can be used.

Data Analysis Details and Signal Processing Approaches

Figure 12:
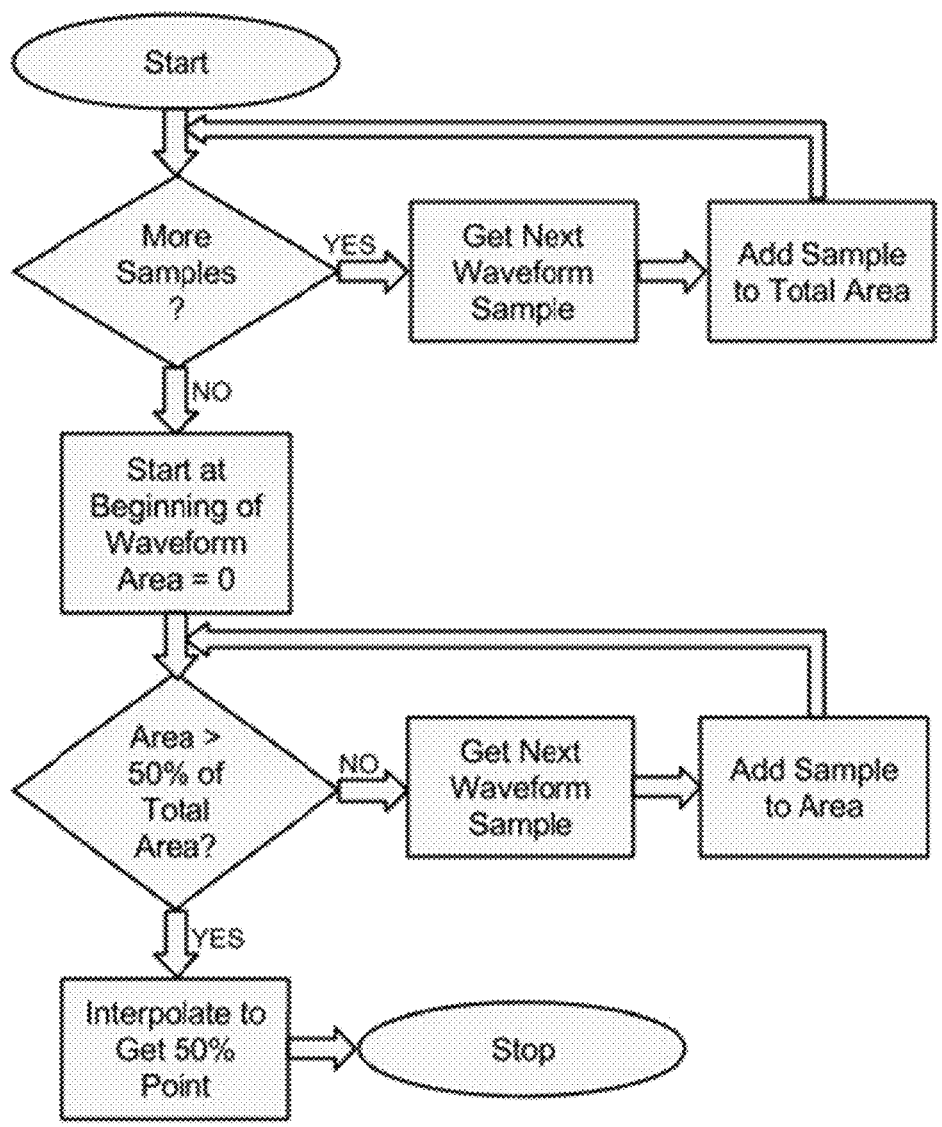
FIG. 12 illustrates a flow diagram of the area-based method for extracting fluorescent lifetime according to one embodiment of the present invention algorithm.

Half-area method: The half area method comprises calculating the center positions of fluorescence and scattering waveforms. The area is calculated by the summation of all the digital values. The precise location where the area reaches half of the total area is extracted and used as the center position of the waveform. The half-area flow diagram is illustrated in FIG. 12. After calculating the total area (the top portion of the flow diagram), the algorithm starts at the beginning of the waveform and calculates the area one sample at a time, detecting when half of the total area is reached or exceeded (middle portion of the flow diagram). It then interpolates between the current sample and previous sample to determine precisely when the area reached half of the total.

Figure 13:
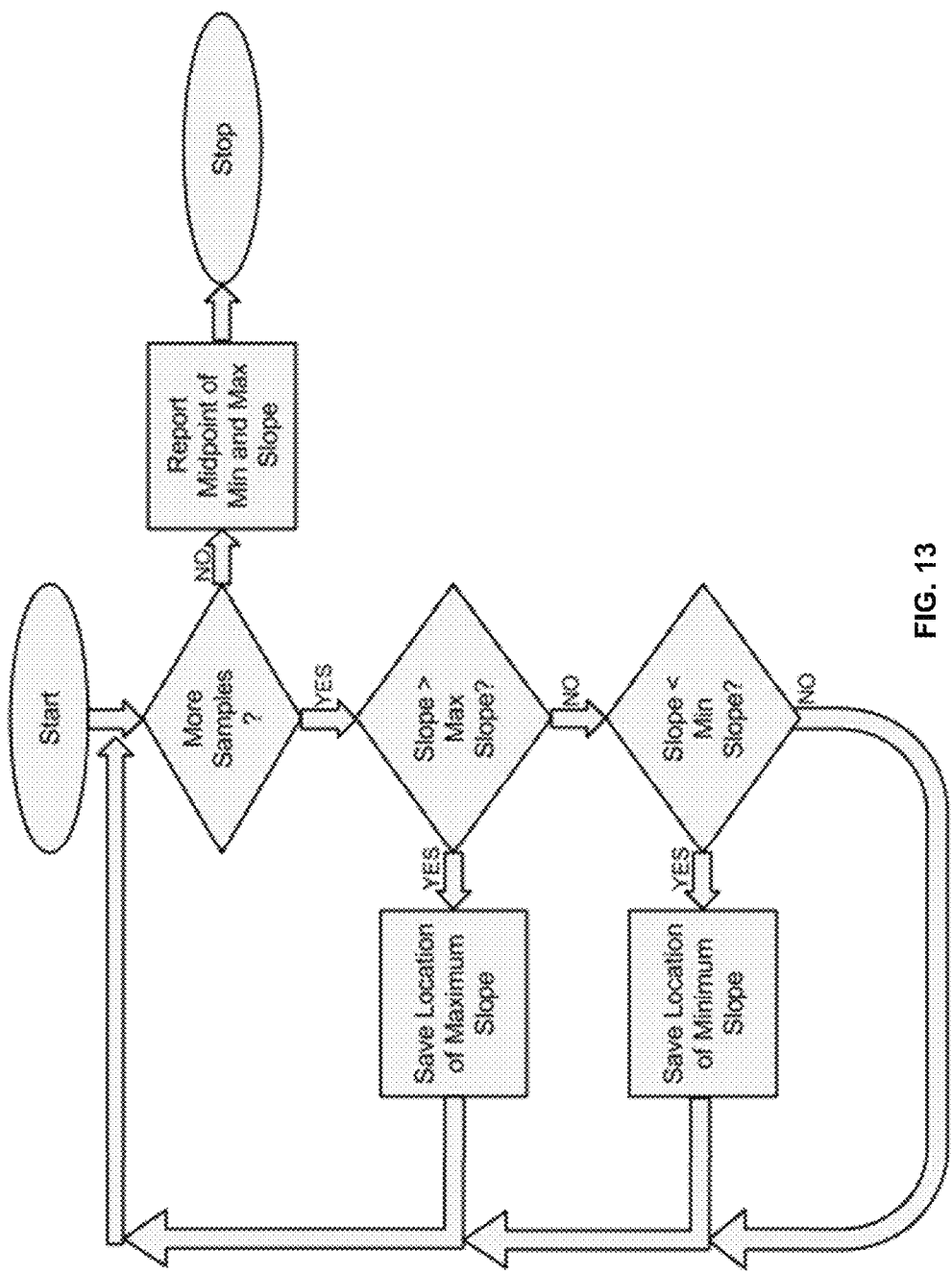
FIG. 13 illustrates a flow diagram of the slope-based method for extracting fluorescent lifetime according to one embodiment of the present invention.

Slope-based method: The slope based method comprises calculating the locations of the steepest rising and falling edges of the waveform, and using the point in between those two locations as the center position of the waveform. The slope-based flow diagram is illustrated in FIG. 13. The slope of the waveform is determined for each sample, and the precise location of the maximum and minimum slopes are determined. The mid-point of these slopes is then calculated and used as the center location.

The fluorescence lifetime was measureable with the different algorithms by implementing three methodologies: (1) generating simulated flow cytometry signals using function generator and delay lines; (2) generating simulated optical signals through a light-emitting diode (LED) to prove the feasibility; and (3) collecting fluorescence lifetime measurements from true fluorescence and side-scatter waveforms from fluorescently labeled microspheres. The signals generated using each approach were collected with a data acquisition system and analyzed according to embodiments of the present invention.

Delay Lines System:

In order to investigate the ability of different algorithms to extract the lifetime, we generated artificial Gaussian signals using a dual channel arbitrary function generator having an average peak voltage of 5-V and average pulse full width at half maximum (FWHM) ranging from 1 μs to 3 μs. The peak voltage was controlled to optimize signals into the digital data system. We synchronously generated two Gaussian signals and delayed them in time (i.e. imparting a simulated lifetime) by adding delay lines. Then, the signals were routed to the two inputs of a high-speed data acquisition system (DAQ). The digitization rate of the DAQ system used was 50 MSPS, which is equivalent to a 20 ns interval between any two adjacent points. In order to simulate actual cytometric transit times we tested different pulse widths and verified with an oscilloscope according to visible tail-to-tail widths. The FWHM observed was 1, 2, and 3-μs. Additionally a range of fluorescence pulse delays between the 'scattering' and 'fluorescence' waveforms was tested by artificially dialing in a delay time on the delay lines to range from 0, 0.7, 3, 5.5, 10.5, 21 to 44.5 ns. The time delays between two Gaussian signals were also verified with an oscilloscope.

LED Hybrid System:

A cross between simulated waveforms and real cytometry waveforms was also used to prove this concept. This compact system was constructed so that standard photomultiplier tubes (PMTs) could be used and allow us to evaluate real pulses using real photodetectors, while still permitting very clean Gaussian-like signals. Therefore, two PMTs were configured to collected light pulses from light emitting diodes that were repetitively pulsed yet delayed in time by amounts typical of real fluorescence decays (i.e. nanoseconds). The LED-based hybrid system is shown in FIG. 3. Two LEDs were pulsed with a dual channel arbitrary function generator and each focused onto a separate PMT. The signals from the two PMTs were pre-amplified by custom-built transimpedance amplifiers with 80 k gain. Then, the signals were routed to the two inputs of the same high-speed data system. The signals from the PMTs were inspected with an oscilloscope and were found to have an approximate 'transit time' of 10 µs. In order to verify the three processing methods, a series of artificial fluorescence pulse delays (FPDs) were introduced by setting the fluorescence pulse delay ("FPD") values between the LED pulses to be 0, 5, 10, 50, and 100 ns. The fluorescence pulse delay is the generic name given to the delay time that is calculated or introduced between two waveforms. The FPD can be thought of as the fluorescence lifetime. It becomes the actual lifetime after calibration steps are performed when real fluorescence microspheres or other samples are measured. For each group of delays, 1000 events were collected and processed.

Figure 6:
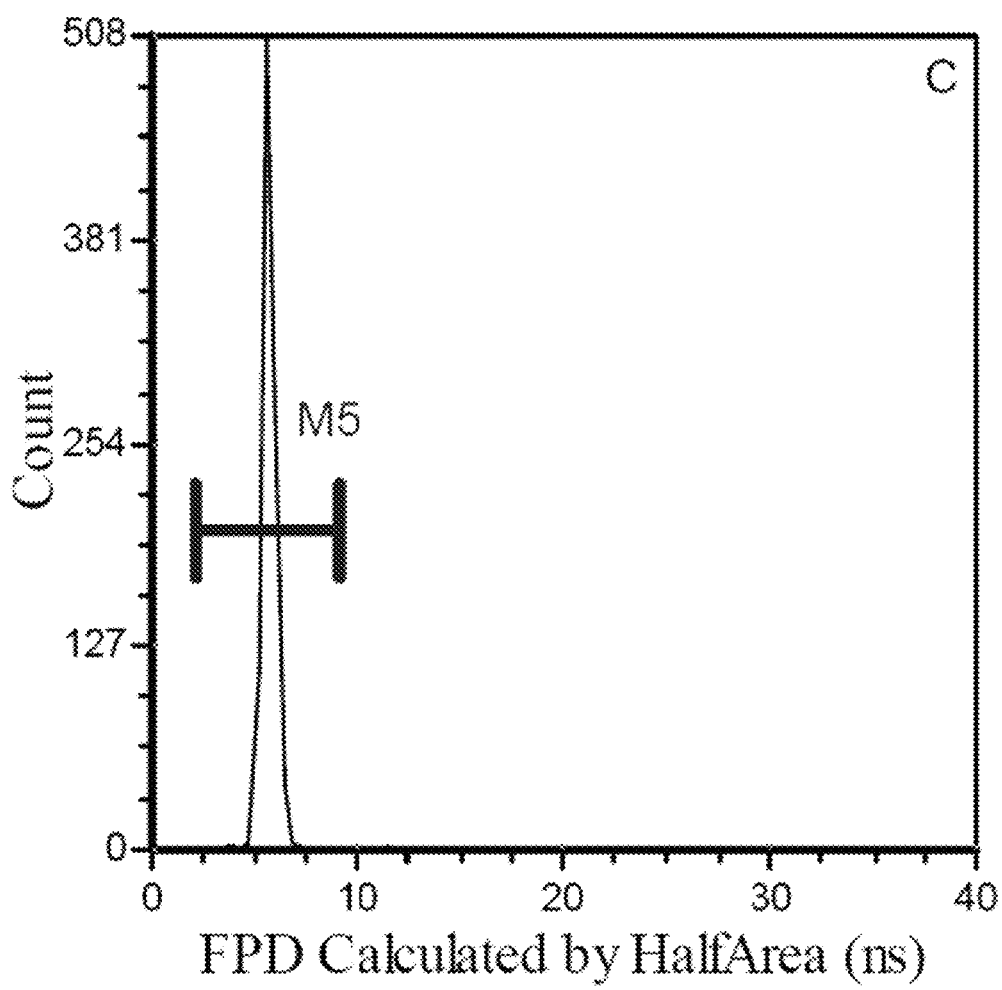
FIG. 6 is a histogram of count vs. FPD having results from the delay lines experiments.

Referring now to FIG. 6, a histogram of the time delay values calculated by the half-area method (in ns) for one set of results from the delay lines experiments is illustrated. For this example, the simulation results chosen were for a "transit time" of 2 microseconds and a simulated FPD of 3 ns, as measured by an oscilloscope (Tektronix, Fort Worth, Tex., TDS 2004B). For the 982 events that fall within the upper and lower bounds of the marker labeled M5, a mean of 5.97 was calculated with a standard deviation of 0.36 ns.

Figure 7:
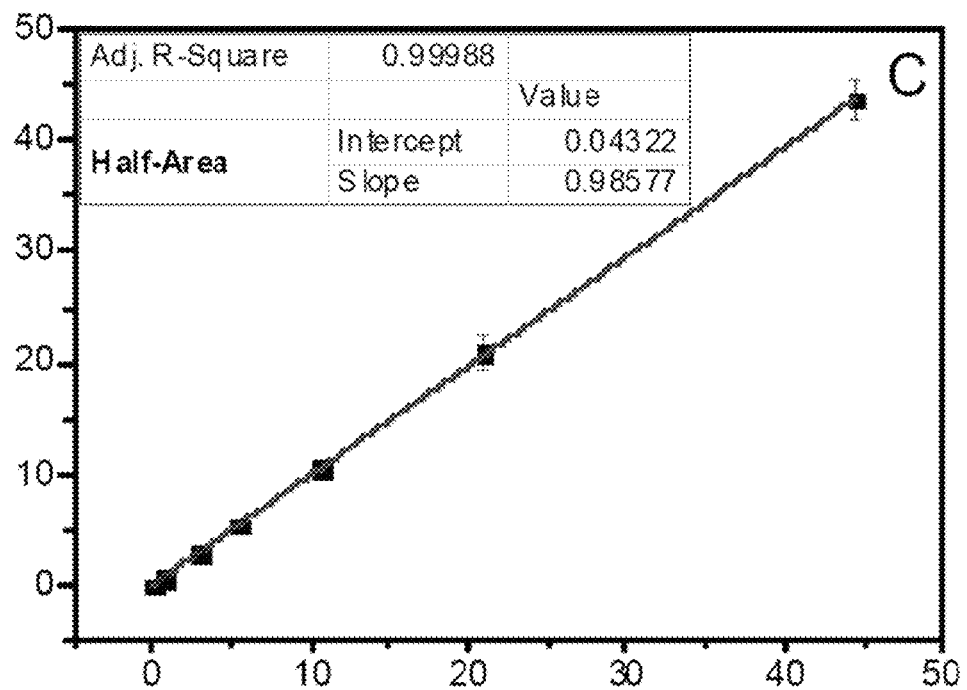
FIG. 7 is a plot comparing the artificially introduced delay values to the actual calculated delay values using the half-area method.

Referring now to FIG. 7 is a plot comparing measured mean delay values (artificial) and standard deviations using the half-area method. Black bars represent the standard deviation for each of the delay experiments. The table in the panel contains the fitting parameters for the linear fit of the data. A linear fitting is applied to evaluate the accuracy of the algorithm. The half-area results demonstrate a small standard deviation, indicating that the delay values are very close to the actual values generated.

Figure 8:
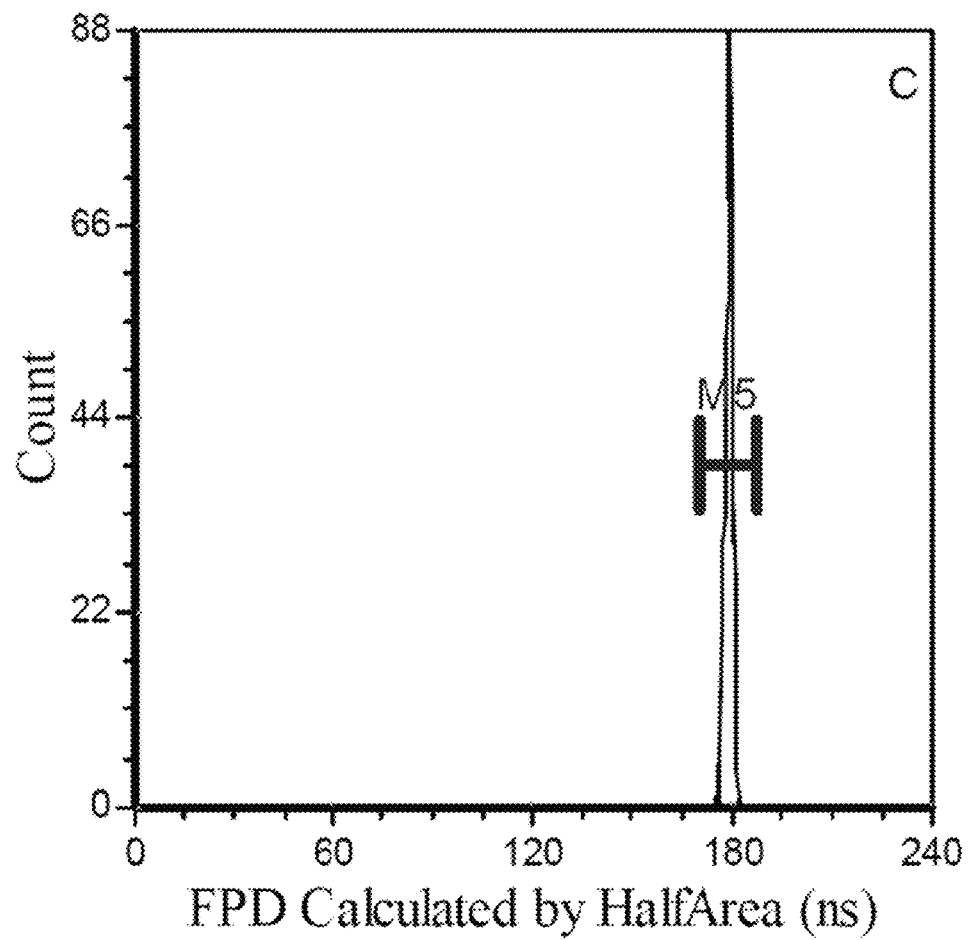
FIG. 8 is a histogram with results from the hybrid-LED cytometry system with the half-area algorithm.

Referring now to FIG. 8 an example histogram collected after artificially introducing delays using the LED-dependent hybrid cytometer is illustrated. The histogram of the time delay values calculated by the half-area method (in ns) for one set of results from the hybrid-LED cytometer supported application of the method. For this example, the simulation results chosen were for a "transit time" of 10 microseconds and a simulated delay of 100 ns, as measured by an oscilloscope. In this example, the delay between mock 'scatter' and 'fluorescence' waveforms was introduced with a function generator and measured to be approximately 100 nanoseconds. The Half-area method resulted in a mean delay of 179.070 ns and 97.33 ns after calibration with a standard deviation of 1.16 ns. For the experiment, a calibration step was performed where 0 nanoseconds of delay were introduced and the inherent delay of the system was measured and the mean value calculated by the half-area method was 81.74 ns. Therefore the delay after calibration can be calculated by the difference: 179.070−81.74=97.33 ns.

Figure 9:
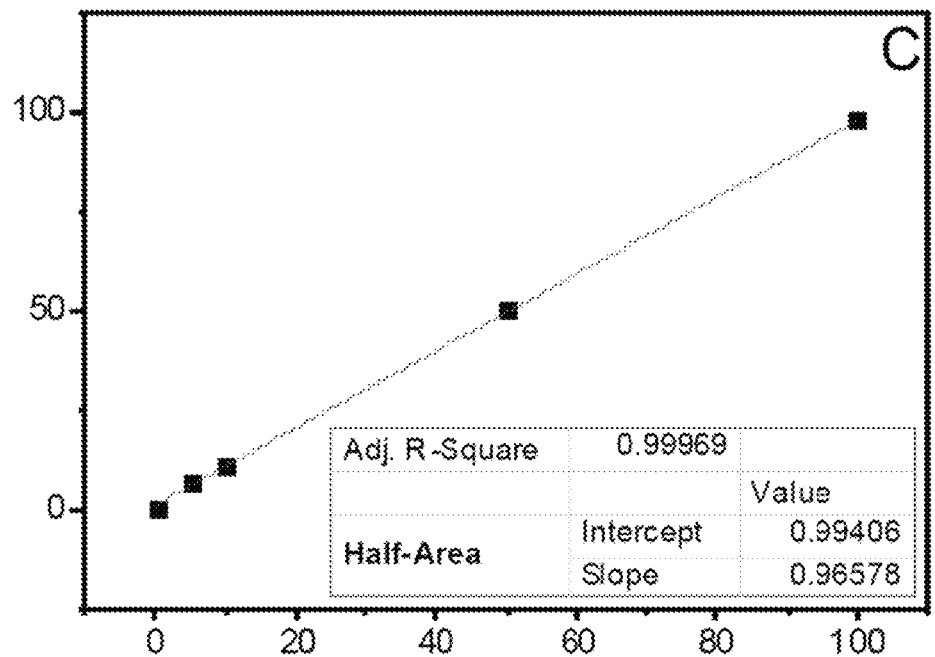
FIG. 9 is a plot comparing the LED-induced delay values to the actual calculated delay values using the half-area method.

Referring now to FIG. 9 is a plot comparing the LED-induced delay values to the actual calculated delay values using the half-area method. Black bars represent the standard deviation for each of the delay experiments. The table in the panel contains the fitting parameters for the linear fit of the data. A linear fitting is also applied to evaluate the accuracy. Application of the half-area method results in small standard deviations indicating that the calculated delay values are close to the real values.

Real Flow Cytometry Samples:

A modified FACSVantage™ SE flow cytometer (Becton Dickinson, CA) with an updated DAQ which has sampling rate of 250 MHz was used for a proof of concept; this approach is an embodiment of the invention. A laser was focused with two crossed cylindrical lenses onto the sample (cells or microspheres) stream. The transit time for each event was found to be approximately 8 µs. Fluorescence and side scatter detection was performed with two photomultiplier tubes focused onto the stream at 90 degrees from the incident laser beam. Upon measurement of the microspheres, both the side scattering and correlated fluorescence signals from each PMT were pre-amplified then directed into respective input channels of the high speed DAQ system.

Calibration steps should be taken for algorithms since the inherent time delays introduced by instruments, methods and cables. For our delay lines and LED experiments, we use the 0 ns delay sets as our reference. The mean delay values collected are recorded as offset and subtracted for the rest of introduced delay experiments. During the experiments, the fluorescein microspheres are used as a reference. The mean delay values collected from this sample are recorded and calibrated to its known fluorescence lifetime. The calibration factor is calculated and used for the rest of fluorescence microspheres.

Fluorescence Samples

Three microspheres with different fluorochromes were used for proof of principle. These microspheres are labeled with Fluorescein (FITC), Phycoerythrin (PE) and Propidium Iodide (PI) respectively. FIG. 10 contains a typical histogram of lifetime results obtained when the waveforms were simulated with a function generator. The example shown is from correlated waveforms with 2 µs transit times, delayed in time from each other by 3 ns. The figure proves that 98.2% of all events under Marker 5 using the Half-area approach have a mean delay value of 5.697 ns and 2.87 ns after calibration with standard deviation of 0.36 ns.

Referring now to FIG. 10 a histogram of delay values calculated based on the half-area method is illustrated. Three markers, M1, M2 and M3, were used to calculate the mean delay values and do statistical analysis of the FITC, PE and PI populations, respectively. Under the markers, we found the mean delay values of FITC, PE and PI calculated from half-area method were 7.832, 5.989 and 21.181 ns, respectively. After calibration based on the known FITC fluorescence lifetime of 4 ns, the mean FPD values of FITC, PE and PI from Half-area method were shifted to 4.0, 2.157 and 17.349 ns with standard deviation of 13.125, 13.926 and 12.362 ns. All the mentioned statistic values are shown in table 3. For example, often real cytometric waveforms have irregular shapes and therefore it is difficult to use different fitting methods to furnish a reliable peak-time value. The half-area based method demonstrated herein is easy; the integration of the noise is often 0, therefore this method might be used in a high noise scenario.

Referring now to FIG. 11 is a table of results from the fluorescent particle study to demonstrate the half-area method. This shows the mean of the measured time delay, the calibrated mean of the measured time delay, and the standard deviation of the time delay measurement.

The preceding examples can be repeated with similar success by substituting the generically or specifically described reactants and/or operating conditions of this invention for those used in the preceding examples.

Note that in the specification and claims, "about" or "approximately" means within twenty percent (20%) of the numerical amount cited. All computer software disclosed herein may be embodied on any non-transitory computer-readable medium (including combinations of mediums), including without limitation CD-ROMs, DVD-ROMs, hard drives (local or network storage device), USB keys, other removable drives, ROM, and firmware.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method for determining an average fluorescent lifetime of a fluorescent particle in a flow cytometer comprising:
    detecting at a first detector a scatter signal and detecting at a second detector a fluorescent signal from a particle as the particle transits within microseconds through an interrogation beam of Gaussian profile emitted from a non-modulated light source having an excitation wavelength that causes the particle to fluoresce in the flow cytometer wherein the first detector and the second detector are temporally phase locked and the interrogation beam has a beam path width that is wider than the fluorescent particle detected;
    digitizing the scatter signal from the first detector and digitizing the fluorescent signal from the second detector with a digitizer having a high sampling rate to produce a digitized scatter waveform and a digitized fluorescence waveform for the fluorescent particle;
    calculating a point on the digitized scatter waveform and a corresponding point on the digitized fluorescence waveform using a same method; and
    determining a time delay if any between the calculated point on the digitized scatter waveform and the calculated point on the digitized fluorescent waveform for the fluorescent particle wherein the time delay is the average fluorescent lifetime of the fluorescent particle and wherein the average fluorescent lifetime is determined as the particle transits through the flow cytometer.

2. The method of claim 1 wherein calculating the point on the digitized scatter waveform and the point on the digitized fluorescence waveform comprises calculating the area of each digitized waveform where the area reaches 50% of the total area for each waveform to determine a 50% point.

3. The method of claim 1 wherein calculating a point on the digitized scatter waveform and calculating the point on the digitized fluorescence waveform comprises calculating the steepest location on the rising edge and falling edge of each waveform with the location in between to determine a peak time point.

4. The method of claim 1 wherein the scatter is a side scatter signal or a forward scatter signal.

5. The method of claim 1 wherein digitizing the scatter signal and the fluorescent signal is an analogue to digital conversion.

6. The method of claim 1 wherein the fluorescent lifetime is a plurality of fluorescent lifetimes from a plurality of fluorophores on or within the fluorescent particle.

7. The method of claim 1 wherein the fluorescent lifetime is from autofluorescence of the particle.

8. The method of claim 1 wherein the particle is a cell.

9. The method of claim 1 wherein the first detector and the second detector is a photo multiplier tube.

10. A method for determining fluorescent lifetime variation between a first fluorescent particle and second fluorescent particle in a flow cytometer comprising:
    detecting at a first detector a scatter signal and detecting at a second detector a fluorescent signal from a first particle and second particle as the first particle and the second particle transits within microseconds through an interrogation beam of Guassian profile emitted from a non-modulated light source having an excitation wavelength that causes the first particle and the second particle to fluoresce in the flow cytometer wherein the first detector and the second detector are temporally phase locked, the interrogation beam has a beam path width that is wider than the first fluorescent particle and the second fluorescent particle detected and wherein a first set of scatter signal and fluorescent signal is generated for the first fluorescent particle and a second set of scatter signal and fluorescent signal is generated for the second fluorescent particle;
    digitizing with a digitizer having a high sampling rate the scatter signal from the first detector and digitizing the fluorescent signal from the second detector for the first fluorescent particle and the second fluorescent particle to produce a first set of digitized scatter waveform and a digitized fluorescence waveform for the first fluorescent particle and a second set of digitized scatter waveform and digitized fluorescence waveform for the second fluorescent particle;
    calculating a point on the digitized scatter waveform and a corresponding point on the digitized fluorescence waveform using a same method for the first set of digitized scatter signal and digitized fluorescent signal and the second set of digitized scatter signal and digitized fluorescent signal;
    determining a first time delay if any between the calculated point on the digitized scatter waveform and the calculated point on the digitized fluorescent waveform of the first fluorescent particle wherein the first time delay is the fluorescent lifetime of the first fluorescent particle and determining a second time delay if any between the calculated point on the digitized scatter waveform and the calculated point on the digitized fluorescent waveform of the second fluorescent particle wherein the second time delay is the fluorescent lifetime of the second fluorescent particle; and
    providing information about the fluorescent lifetime of the second fluorescent particle as compared to the fluorescent lifetime of the first fluorescent particle as the second particle transits through the flow cytometer.

11. The method of claim 10 wherein calculating the point on the digitized scatter waveform and the point on the digitized fluorescence waveform comprises calculating the area on each digitized waveform where the area reaches 50% of the total area for each waveform is the 50% point.

12. The method of claim 10 wherein calculating a point on the digitized scatter waveform and calculating the point on the digitized fluorescence waveform comprises calculating the steepest location on the rising edge and falling edge of each waveform with the location in between as the peak time point.

13. The method of claim 10 wherein the fluorescent lifetime is a plurality of fluorescent lifetimes from a plurality of fluorophores on or within the fluorescent particle.

14. The method of claim 10 wherein the fluorescent lifetime is from autofluorescence of the particle.

15. The method of claim 10 wherein the particle is a cell.

16. The method of claim 10 wherein the first detector and the second detector is a photo multiplier tube.

17. A non-transitory computer-readable storage medium containing an executable program for causing a processor to execute a method for determining fluorescent lifetime variation between a first fluorescent particle and second fluorescent particle in a flow cytometer wherein the method comprising:

obtaining a digitized scatter waveform and a digitized fluorescence waveform for a first fluorescent particle to create a first set of digitized data and obtaining a digitized scatter waveform and a digitized fluorescence waveform for a second fluorescent particle to create a second set of digitized data collected from a first particle and a second particle transiting through an interrogation beam of Guassian profile emitted from a non-modulated light source having an excitation wavelength that causes the first particle and the second particle to fluoresce in the flow cytometer;

calculating a point on the digitized scatter waveform and a corresponding point on the digitized fluorescence waveform using a same method for the first set of digitized scatter signal and fluorescent signal and the second set of digitized scatter signal and fluorescent signal;

determining the time delay if any between the calculated point on the digitized scatter waveform and the calculated point on the fluorescent waveform of the first fluorescent particle to determine the fluorescent lifetime of the first fluorescent particle;

determining the time delay if any between the calculated point on the digitized scatter waveform and the calculated point on the fluorescent waveform of the second fluorescent particle to determine the fluorescent lifetime of the second fluorescent particle; and providing information regarding the fluorescent lifetime of the second fluorescent particle as compared to the lifetime of the first fluorescent particle after the digitized scatter waveform and the digitized fluorescence waveform is obtained from the second fluorescent particle.

18. The method of claim 17 wherein the code for calculating the point on the digitized scatter waveform and the point on the digitized fluorescence waveform comprises calculating the area on each digitized waveform where the area reaches 50% of the total area for each waveform is the 50% point.

19. The method of claim 17 wherein the code for calculating a point on the digitized scatter waveform and calculating the point on the digitized fluorescence waveform comprises calculating the steepest location on the rising edge and falling edge of each waveform with the location in between as the peak time point.

* * * * *